United States Patent [19]
Cabri et al.

[11] Patent Number: 5,902,902
[45] Date of Patent: May 11, 1999

[54] PROCESS FOR THE INDUSTRIAL PREPARATION OF AMINOACETYLENES

[75] Inventors: Walter Cabri, Rozzano; Erminio Oldani, Sedriano, both of Italy

[73] Assignee: Secifarma S.p.A., Milan, Italy

[21] Appl. No.: 09/025,263

[22] Filed: Feb. 18, 1998

[30] Foreign Application Priority Data

Oct. 10, 1997 [IT] Italy ................................. MI97A2301

[51] Int. Cl.$^6$ ................................................. C07C 209/02
[52] U.S. Cl. ............................................................ 564/409
[58] Field of Search ............................................. 564/409

[56] References Cited

PUBLICATIONS

Bleicher et al., Synlett (11), 115–116, 1995.

*Primary Examiner*—Brian M. Burn
*Attorney, Agent, or Firm*—Griffin, Butler Whisenhunt & Szipl, LLP

[57] ABSTRACT

A process for the preparation of 3-aminophenylacetylene derivatives of formula:

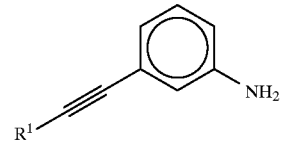

wherein $R_1$ is as defined in the disclosure

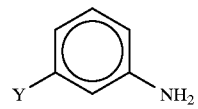

wherein Y is as defined in the disclosure

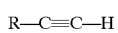

wherein R is as defined in the disclosure.

9 Claims, No Drawings

PROCESS FOR THE INDUSTRIAL PREPARATION OF AMINOACETYLENES

The present invention relates to a process for the preparation of 3-aminophenylacetylenes based on the condensation between variously substituted acetylenes and 3-bromo or 3-iodo aniline catalyzed by palladium complexes.

3-Amino-phenyl acetylenes derivatives have been claimed and synthesized as herbicides in U.S. Pat. No. 4,305,751, U.S. Pat. No. 4,362,551, U.S. Pat. No. 4,361,440. Moreover, aminophenylacetylenes were used at the end position in polyamide resins which are stable at high temperatures (higher than 450° C.), as described in U.S. Pat. No. 3,845,018 and U.S. Pat. No. 3,879,349. Phenylacetylenes with antithrombotic and antiinflammatory activities have been claimed in U.S. Pat. No. 3,968,251, U.S. Pat. No. 3,991,212, U.S. Pat. No. 3,852,364; in WO963034 3-aminophenyl acetilenes derivatives have been described to have anticancer activity.

The synthesis of 3-aminophenylacetylene has been described in a number of publications and patents, the most efficient methods being based on three main reactions:

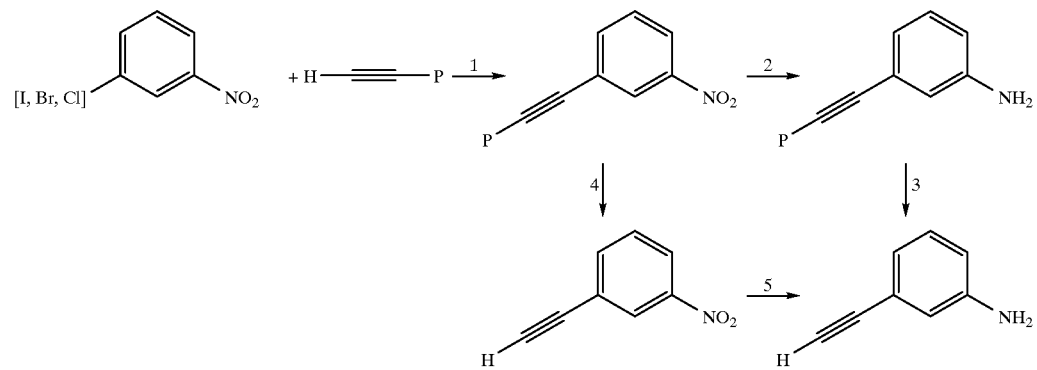

P=protective group

1—Step 1: synthesis of a 3-nitrophenylacetylene derivative by means of a palladium/copper catalyzed reaction between 3-NO$_2$-phenyl- bromide or iodide and a protected acetylene. The use of products of the type 2-methyl-3-butynol has been disclosed and claimed in U.S. Pat. No. 4,204,078, whereas the use of silylated derivatives, such as trimethylsilylacetylene, has been described and claimed in U.S. Pat. No. 4,465,833 and in the publication *Journal of Organic Chemistry* 1981, 46, 2280.

2—Step 2 or 5: selective reduction of the nitro group in the presence of the triple bond. The methods based on the use of FeSO$_4$ (U.S. Pat. No. 3,845,018), NaHSO$_3$ (U.S. Pat. NO. 3,975,444), Zn/NH$_3$ (Tetrahedron 1959, 340) are not industrially applicable due to their high environmental impact, to the high dilutions and/or large excess of reducer required and/or to the difficult recovery of the end product.

An alternative to these processes, which minimizes the environmental impact of the production, is the catalytic reduction of the nitro derivative, which can be used only in the case of protected aminophenylacetylenes (step 2) U.S. Pat. No. 4,139,561, U.S. Pat. No. 4,215,226, U.S. Pat. No. 4,051,177, U.S. Pat. No. 4,219,679, *Journal of Organic Chemistry* 1979, 44, 3671, ibid 1979, 44, 1233. A number of hydrogenation catalysts have been: Os/BaSO$_4$, Ru/C, Rh/alumine, PtO$_2$, Raney Ni, RuS$_2$, CoS$_X$. Anyhow, independently of the catalyst, the reaction involves a number of chemoselectivity problems, and generally side-products from the reduction of the triple bond are never completely avoided. Moreover, some difficulties in the industrialization process exist.

3—Step 3 or 4: cleavage of the acetylene protecting-group. For products of the 2-methyl-3-butynol type: *Journal of Organic Chemistry* 1979, 44, 3671, ibid. 1979, 44, 1233, Prep. Div. J. Chem. Am. Chem. Soc. 1979, 24, 233. For silylated derivatives: *Journal of Organic Chemistry* 1981, 46, 2280.

The Pd/Cu complexes catalyzed reaction between 3-bromo or 3-iodoaniline and the protected acetylene would eliminate the difficult process for the chemoselective reduction of the nitro group thereby obtaining the product in only 2 steps.

The reaction carried out according to the methods used in literature for analogous products (J. Org. Chem. 1989, 54, 1218) yields poor results. A low conversion is in fact observed. High conversions are obtained only increasing the amount of the catalyst, thus making the process costs higher. Moreover, a number of purification steps are required to obtain a highly pure product.

Surprisingly, it has been found that 3-aminophenylacetylene derivatives protected at the triple bond can be prepared in high yield (>70) and purity (>98%) using commercially available starting products such as bromo- or iodo- aniline, carrying out the palladium and copper complexes catalyzed reaction in the presence of a strong organic base. More specifically, the use of 1,1,3,3-tetramethyl guanidine allows to use minimum amounts, i.e. ≦1 mol %, of the expensive palladium complex. Other amines which can be conveniently used comprise diazabicyclooctane (DBO), diazabicycloundecane (DBU) and the like.

The process according to the invention is illustrated in the following scheme:

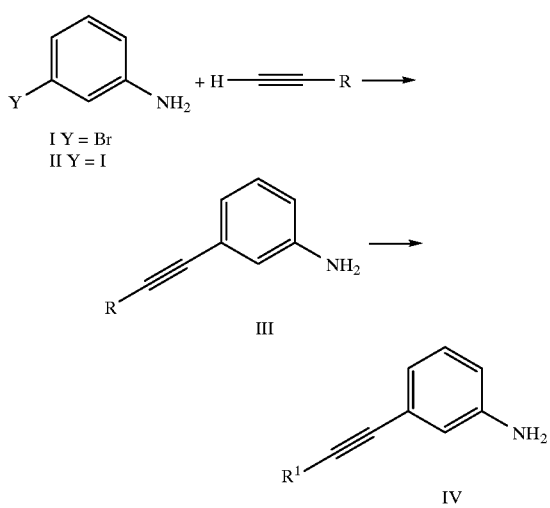

I Y = Br
II Y = I in which R is an easily removable group or an optionally substituted $C_1$–$C_6$ alkyl group, or optionally substituted phenyl, whereas $R_1$ is hydrogen or has the same meanings as R.

Examples of easily removable groups comprise trialkylsilyl groups such as trimethylsilyl or $R_2C(OH)$ such as $(CH_3)_2C(OH)$. Examples of optionally substituted alkyl or phenyl groups comprise methyl, ethyl, 1-hydroxy-2-propyl, in particular, R and $R_1$ can have the meanings corresponding to the compounds disclosed in the above cited U.S. patents.

The palladium catalyst can be used in any molar ratio to the product, but usually the palladium amount is $\leq 1$ mol % to make the process efficient and not very expensive.

Different palladium catalysts or pre-catalysts can be used:

$L_2PdX_2$: wherein L is a monodentated phosphine of the type PRR'R" wherein R, R' and R" can be independently phenyl, alkyl $C_1$–$C_4$, cyclohexyl or a substituted aromatic group; wherein X is an anionic binder such as Cl, Br, I, CN, OAc, acetyl acetonate.

L⌒L $PdX_2$: wherein L⌒L can be a bidentated phosphine such as bisdiphenylphosphino methane, 1,2-bisdiphenylphosphino ethane, 1,2-bisdiphenylphosphino ethylene, 1,3-bisdiphenylphosphino propane, 1,4-bisdiphenylphosphino butane, 1,1'-bisdiphenylphosphino ferrocene or a bidentated nitrogen binder such as 1,10-phenanthroline, 2,9-dimethyl-1,10-phenanthroline; wherein X is an anionic binder such as Cl, Br, I, OAc, acetyl acetonate.

$PdL_4$: wherein L is a monodentated phosphine of the type PRR'R" wherein R, R' and R" can be independently phenyl, $C_1$–$C_4$ alkyl, cyclohexyl or a substituted aromatic group.

The palladium catalyst can be generated in situ from $PdX_2+L_n$: wherein X is an anionic binder such as Cl, Br, I, OAc; wherein L is a monodentated phosphine of the type PRR'R" wherein R, R' and R" can be independently phenyl, $C_1$–$C_4$ alkyl, cyclohexyl or a substituted aromatic group or a bidentated phosphine such as bisdiphenylphosphino methane, 1,2-bisdiphenylphosphino ethane, 1,2-bisdiphenylphosphino ethylene, 1,3-bisdiphenylphosphino propane, 1,4-bisdiphenylphosphino butane, 1,1'-bisdiphenylphosphino ferrocene or a bidentated nitrogen binder such as 1,10-phenanthroline, 2,9-dimethyl-1,10-phenanthroline.

The palladium catalyst can be generated in situ from $Pd_2$(dibenzylydeneacetone)$_3$ or $Pd_2$(dibenzylydeneacetone)$_3CHCl_3+L_n$: wherein L is a monodentated phosphine of the type PRR'R" wherein R, R' and R" can be independently phenyl, $C_1$–$C_4$ alkyl, cyclohexyl or a substituted aromatic group or a bidentated phosphine such as bisdiphenylphosphino methane, 1,2-bisdiphenylphosphino ethane, 1,2-bisdiphenylphosphino ethylene, 1,3-bisdiphenylphosphino propane, 1,4-bisdiphenylphosphino butane, 1,1'-bisdiphenylphosphino ferrocene or a bidentated nitrogen binder such as 1,10-phenanthroline, 2,9-dimethyl-1,10-phenanthroline.

The copper(I) catalyst can be of the type CuX with X=Cl, Br, I, acetate, CN.

The reaction can be carried out either in the absence or in the presence of organic solvents such as DMF, N-methyl pyrrolidone, toluene, dioxane, DMSO or mixtures thereof. Temperature can range from 20° C. to 200° C.

Any transformations of compound (III) into compound (IV) can be effected according to conventional methods, for example by removing the removable group, by selective hydrogenation, by acidification or similar known methods for removing protective groups from triple bonds.

The process described has a number of advantages compared with the processes for the selective reduction of the nitro group: there are no problems from the industrial point of view, the starting products are commercially available, hydrogen is not used thereby gaining safety, a lower number of steps are required compared with the known syntheses thus increasing the yields, no complex purification steps are necessary, thanks to the high selectivity of the reaction.

EXAMPLE 1

4 (3-aminophenyl)-2-methyl-3-butyn-2-ol

A 250 ml round bottomed flask fitted with refrigerator, under nitrogen stream, is loaded with 3-bromoaniline (16 ml), dimethylformamide (80 ml), 2-methyl-3-butyn-2-ol (21.3 ml), 1,1,3,3-tetramethyl guanidine (20.3 ml), CuCl (0.044 g), $PdCl_2$ (0.156 g) and triphenyl phosphine (0.925 g), in this order. The mixture is heated to 70°–75° C., keeping this temperature until completion of the reaction. $H_2O$ (250 ml) and $CH_2Cl_2$ (100 ml) are added at a temperature of 35°–30° C. The organic phase is dried, then evaporated to dryness. The residue is purified by chromatography to obtain 18.5 g of 4-(3-aminophenyl)-2-methyl-3-butyn-2-ol. Yield: 71% with HPLC purity $\geq 99\%$.

EXAMPLE 2

The procedure described in example 1 is followed, using 3-iodoaniline instead of 3-bromoaniline. Yield 73%, HPLC purity $\geq 99\%$.

EXAMPLE 3

The procedure described in example 1 is followed, using the preformed $PdCl_2(PPh_3)$ complex instead of $PdCl_2$ and triphenylphosphine. Yield 71%, HPLC purity $\geq 99\%$.

EXAMPLE 4

The procedure described in example 1 is followed, using 1,1'-bis-diphenylphosphino ferrocene instead of triphenylphosphine as the binder and N-methylpyrrolidone as the solvent. Yield 75%, HPLC purity $\geq 99\%$.

EXAMPLE 5

The procedure described in example 1 is followed, using CuBr instead of CuCl as the copper salt. Yield 74%, HPLC purity $\geq 99\%$.

EXAMPLE 6

The procedure described in example 1 is followed, using CuI instead of CuCl as the copper salt. Yield 75%, HPLC purity $\geq 99\%$.

EXAMPLE 7

The procedure described in example 1 is followed, using toluene under reflux with CuCN instead of CuCl as the solvent. Yield 70%, HPLC purity ≧99%.

EXAMPLE 8

The procedure described in example 1 is followed, using no solvent. Yield 78%, HPLC purity ≧99%.

EXAMPLE 9

The procedure described in example 1 is followed, using 1,4-diazabicyclo[2,2,2]octane instead of 1,1,3,3-tetramethyl guanidine as the base. Yield 65%, HPLC purity ≧99%.

EXAMPLE 10

The procedure described in example 1 is followed, using Pd(OAc)$_2$ instead of PdCl$_2$ and N-methylpyrrolidone as the solvent. Yield 70%, HPLC purity ≧99%.

EXAMPLE 11

The procedure described in example 1 is followed, using palladium tetrakistriphenylphosphine instead of PdCl$_2$ and triphenylphosphine as the catalyst. Yield 74%, HPLC purity >99%.

The product obtained in the examples 1 to 9 can be transformed into 3-amino-phenylacetylene by a simple treatment with NaOH in toluene as described in J. Org. Chem. 1979, vol. 44, 1233.

EXAMPLE 12

3-aminophenyl-trimethylsilylacetylene

A 250 ml round bottomed flask, fitted with refrigerator, under a nitrogen stream, is loaded with 3-bromoaniline (2 ml), dimethylformamide (10 ml), trimethylsilylacetylene (3.4 ml), 1,1,3,3-tetramethyl guanidine (2.5 ml), CuCl (3.6 mg), PdCl$_2$ (9.7 mg) triphenyl phosphine (58 mg), in this order. The mixture is heated to 55°–57° C. keeping this temperature until completion of the reaction. H$_2$O (50 ml) and ACOEt (50 ml) are added at a temperature of 35°–30° C. The organic phase is evaporated to dryness and the residue is dissolved in CH$_3$OH (10 ml) and 50% HCl (10 ml) is heated to 40–50° C. for two hours. Methanol is evaporated off and the residual mixture is treated with NaOH, extracted with toluene. The organic phase is dried, and the solvent removed under vacuum affording 3-amino-phenyl acetylene.

We claim:

1. A process for the preparation of 3-aminophenylacetylene derivatives of formula:

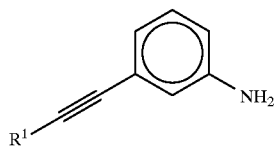

wherein R$_1$ is hydrogen, optionally substituted C$_1$–C$_6$ alkyl or optionally substituted phenyl, which comprises the reaction of a 3-haloaniline of formula

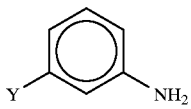

wherein Y is chlorine, bromine or iodine with an acetylene derivative of formula

wherein R is an easily removable protecting group or an optionally substituted C$_1$–C$_8$ alkyl group or optionally substituted phenyl,
in the presence of palladium and copper complexes and of a strong organic base, optionally followed by removal of the protective group.

2. A process according to claim 1 wherein the base is selected from the group consisting of diazabicyclooctane, diazabicycloundecane, and 1,1,3,3-tetramethylguanidine.

3. A process according to claim 2 in which the base is 1,1,3,3-tetramethylguanidine.

4. A process according to claim 1 in which the palladium catalyst is selected from the group consisting of compounds of the formulas:

L$_2$PdX$_2$: wherein L is a monodentated phosphine of the type PRR'R" wherein R, R' and R" are independently phenyl, C$_1$–C$_4$ alkyl, cyclohexyl, or a substituted aromatic group; wherein X is an anionic binder selected from the group consisting of Cl, Br, I, CN, OAc, and acetylacetonate;

L∩LPdX$_2$: wherein L∩L is a bidentated phosphine selected from the group consisting of bisdiphenylphosphino methane, 1,2-bisdiphenylphosphino ethane, 1,2-bisdiphenylphosphino ethylene, 1,3-bisdiphenylphosphino propane, 1,4-bisdiphenylphosphino butane, and 1,1'-bisdiphenylphosphino ferrocene or a bidentated nitrogen binder selected from the group consisting of 1,10-phenanthroline and 2,9-dimethyl-1,10-phenanthroline; wherein X is an anionic binder selected from the group consisting of Cl, Br, I, OAc, and acetylacetonate; and PdL$_4$: wherein L is a monodentated phosphine of the type PRR'R" wherein R, R' and R" are independently phenyl, C$_1$–C$_4$ alkyl, cyclohexyl, or a substituted aromatic group.

5. A process according to claim 1 in which the palladium catalyst is generated in situ from PdX$_2$+L$_n$: wherein X is an anionic binder selected from the group consisting of Cl, Br, I, and OAc; and wherein L is a monodentated phosphine of the type PRR'R" wherein R, R', and R" are independently phenyl, C$_1$–C$_4$ alkyl, cyclohexyl, or a substituted aromatic group or L is a bidentated phosphine selected from the group consisting of bisdiphenylphosphino methane, 1,2-bisdiphenylphosphino ethane, 1,2-bisdiphenylphosphino ethylene, 1,3-bisdiphenylphosphino propane, 1,4-bisdiphenylphosphino butane, and 1,1'-bisdiphenylphosphino ferrocene or a bidentated nitrogen binder selected from the group consisting of 1,10-phenanthroline and 2,9-dimethyl-1,10-phenanthroline.

6. A process according to claim 1 in which the palladium catalyst is generated in situ from Pd$_2$(dibenzylydeneacetone)$_3$ or Pd$_2$(dibenzylydeneacetone)$_3$ CHCl$_3$+L$_n$: wherein L is a monodentated phosphine of the type PRR'R" wherein R, R' and R" are independently phenyl, C$_1$–C$_4$ alkyl, cyclohexyl, or a substituted aromatic group or L is a bidentated phosphine selected from the group consisting of bisdiphenylphosphino methane, 1,2-bisdiphenylphosphino ethane, 1,2-bisdiphenylphosphino ethylene, 1,3-bisdiphenylphosphino propane, 1,4-bisdiphenylphosphino butane, and 1,1'-bisdiphenylphosphino ferrocene or a bidentated nitrogen binder selected from the group consisting of 1,10-phenanthroline and 2,9-dimethyl-1,10-phenanthroline.

7. A process according to claim 1 in which the copper(I) catalyst is selected from the group consisting of cuprous cyanide, acetate, iodide, bromide, and chloride.

8. A process according to claim 1 in which the reaction is carried out in solvents selected from the group consisting of dimethylformamide, N-methyl-pyrrolidone, toluene, dioxane, dimethylsulfoxide, and mixtures thereof.

9. A process according to any one of the above claims for the preparation of 4-(3-aminophenyl)-2-methyl-3-butyn-2-ol.

* * * * *